US009805159B2

(12) United States Patent
Behrouz et al.

(10) Patent No.: US 9,805,159 B2
(45) Date of Patent: Oct. 31, 2017

(54) SIMULATION ENVIRONMENT FOR EXPERIMENTAL DESIGN

(71) Applicant: NEUROINITIATIVE, LLC, Jacksonville, FL (US)

(72) Inventors: Bahareh Behrouz, Jacksonville Beach, FL (US); Andrew David Lee, Jacksonville Beach, FL (US)

(73) Assignee: NEUROINITIATIVE, LLC, Jacksonville, FL (US)

( * ) Notice: Subject to any disclaimer, the term of this patent is extended or adjusted under 35 U.S.C. 154(b) by 0 days.

(21) Appl. No.: 14/790,400

(22) Filed: Jul. 2, 2015

(65) Prior Publication Data

US 2017/0004253 A1  Jan. 5, 2017

(51) Int. Cl.
| | |
|---|---|
| G01N 33/48 | (2006.01) |
| G01N 33/50 | (2006.01) |
| G06F 19/12 | (2011.01) |
| G06F 19/24 | (2011.01) |
| G06F 19/28 | (2011.01) |

(52) U.S. Cl.
CPC .............. *G06F 19/12* (2013.01); *G06F 19/24* (2013.01); *G06F 19/28* (2013.01)

(58) Field of Classification Search
None
See application file for complete search history.

(56) References Cited

U.S. PATENT DOCUMENTS

| | | | |
|---|---|---|---|
| 2004/0029149 A1* | 2/2004 | Palsson .................. | G06F 19/12 435/6.14 |
| 2005/0119837 A1* | 6/2005 | Prakash .................. | G06F 19/28 702/27 |
| 2005/0228592 A1* | 10/2005 | Ahuja ................ | G01N 33/6803 702/19 |
| 2007/0233441 A1 | 10/2007 | Crowley, Jr. et al. | |
| 2014/0288910 A1 | 9/2014 | Chandra et al. | |
| 2015/0178443 A1 | 6/2015 | Tertiaux et al. | |

FOREIGN PATENT DOCUMENTS

| | | |
|---|---|---|
| JP | 2014-211907 | 11/2014 |
| WO | WO 02/063479 A1 * | 8/2002 |
| WO | WO 03/007217 | 1/2003 |

OTHER PUBLICATIONS

Swope et al. A computer simulation method for the calculation of equilibrium constants for the formation of physical clusters of molecules: Application to small water clusters. The Journal of Chemical Physics, 1982, vol. 76, pp. 637-649.*

Blinov, ML et al. "Complexity and modularity of intracellular networks—A systematic approach for modelling and simulation" *IET Syst Biol.*, 2008, 2(5):363-368.

Brown, SA and Loew, LM "Computational analysis of calcium signaling and membrane electrophysiology in cerebellar Purkinje neurons associated with ataxia" *BMC Syst Biol.*, 2012, 6:70, pp. 1-20.

Brown, SA et al. "Virtual Neuron: a strategy for merged biochemical and electrophysiological modeling" *Comput Neurosci.*, 2011, 31(2):385-400.

Cowan, AE et al. "Spatial modeling of cell signaling networks" *Methods Cell Biol.*, 2012, 110:195-221.

Cowan, AE et al. "Using the Virtual Cell Simulation Environment for Extracting Quantitative Parameters from Live Cell Fluorescence Imaging Data" *Microsc. Microanal.*, 2009, 15(Suppl 2):1522-1523.

Ditlev, JA et al. "An open model of actin dendritic nucleation" *Biophys J.*, 2009, 96:3529-3542.

Ditlev, JA et al. "Stoichiometry of Nck-dependent actin polymerization in living cells" *J Cell Biol*, 2012, 197(5):643-658.

Kerr, R et al. "Fast Monte Carlo Simulation Methods for Biological Reaction-Diffusion Systems in Solution and on Surfaces" *SIAM J. Sci. Comput.*, 2008, 30(6):3126-3149.

Loew, LM "The Virtual Cell project" *Novartis Found Symp.*, 2002, 247:151-160; discussion 160-161, 198-206, 244-252, abstract only.

Loew, LM and Schaff, JC "The Virtual Cell: A software environment for computational cell biology" *Trends in Biotechnology*, 2001, 19(10):401-406.

Michalski, PJ and Loew, LM "CaMKII activation and dynamics are independent of the holoenzyme structure: an infinite subunit holoenzyme approximation" *Phys Biol.*, 2012, 9(3):036010, 25 pages.

Moraru, I et al. "The virtual cell modelling and simulation software environment" *IET Syst Biol.*, 2008, 2(5):352-362.

Moraru, I et al. "The virtual cell: An integrated modeling environment for experimental and computational cell biology" *Ann NY Acad Sci.*, 2002, 971:595-596.

Moraru, I. et al. "Think simulation—think experiment: the Virtual Cell paradigm" In Proceedings of the 2006 Winter Simulation Conference, vol. 38, L.F. Perrone, F. Wieland, J. Liu, B. Lawson, D. Nicol, and R. Fujimoto, editors. IEEE Proceedings, Monterey, CA., 2006, pp. 1713-1719.

Novak, IL et al. "Diffusion in cytoplasm: Effects of excluded volume due to internal membranes and cytoskeletal structures" *Biophysical Journal*, 2009, 97(3):758-767.

(Continued)

*Primary Examiner* — Russell S Negin
(74) *Attorney, Agent, or Firm* — Saliwanchik, Lloyd & Eisenschenk

(57) ABSTRACT

Techniques and systems are disclosed for enabling a simulation environment for experimental design. The interactions of a configuration of molecules inside a biological structure or system, such as a cell (e.g., a neuron) or virtual test tube, are modeled using message-based techniques to communicate between molecules proximal to one another in a virtual 3-D geometric space. Some techniques and systems allow distributed processing of the individual molecular interactions across a plurality of work nodes. Some techniques and systems allow the storage of detailed information about the current state of the simulation of the biological model for each discrete time slice. This enables the ability for a 4-D playback/review of any particular spatial or temporal focus area of the simulation.

22 Claims, 4 Drawing Sheets

(56) References Cited

OTHER PUBLICATIONS

Novak, IL et al. "Quantitative analysis of G-actin transport in motile cells" *Biophys J.,* 2008, 95(4):1627-1638.
Schaff, JC et al. "Physiological Modeling with the Virtual Cell Framework" In Methods in Enzymology, M. Johnson and L. Brand, Eds. Academic Press, San Diego, 2000, vol. 321, pp. 1-23.
Slepchenko, BM and Loew, LM "Use of Virtual Cell in Studies of Cellular Dynamics" *International Review of Cell and Molecular Biology,* 2010, 283:1-56.
Slepchenko, BM et al. "Computational cell biology: Spatiotemporal simulation of cellular events" *Annual Review of Biophysics & Biomolecular Structure,* 2002, 31:423-441.
Slepchenko, BM et al. "Quantitative Cell Biology with the Virtual Cell" *Trends in Cell Biology,* 2003, 13(11):570-576.
Stefan, MI et al. "Multi-state Modeling of Biomolecules" *PLoS Comput Biol,* 2014, 10(9):e1003844, 9 pages.
Stiles, JR and Bartol, TM "Monte Carlo methods for simulating realistic synaptic microphysiology using MCell" In: Computational Neuroscience: Realistic Modeling for Experimentalists, Erik De Schutter, Ed., CRC Press, Boca Raton, 2001, pp. 87-127.
Stiles, JR et al. "Miniature endplate current rise times <100 μs from improved dual recordings can be modeled with passive acetylcholine diffusion from a synaptic vesicle" *Proc. Natl. Acad. Sci. USA,* 1996, 93:5747-5752.

* cited by examiner

SIMULATION ENVIRONMENT FOR EXPERIMENTAL DESIGN

BACKGROUND OF THE INVENTION

The drug development timeline currently takes approximately 15 years and over $1.2 billion dollars for a successful nervous system drug. At every stage of this lengthy and expensive process, from laboratory research to clinical trials, there is a high failure rate due to unforeseen biological interactions. In the case of degenerative diseases such as Alzheimer's or Parkinson's disease, no drug has yet been able to stop the progressive degeneration of neurons, and most drugs only ameliorate the symptoms rather than impact the disease process. While the rate of biological research, particularly in the field of neuroscience, has grown tremendously, neuroscientists have been limited by the availability of computational tools that allow them to put together the data in a cohesive manner. The fact that the bottleneck of research has become understanding and predicting interactions is a major problem for the field.

Computational tools that simulate molecular interactions within neurons are very limited. In fact, most neuroscientists today use static pathway maps such as KEGG (Kyoto Encyclopedia of Genes and Genomes) Pathways to visualize the molecular interactions within the neuron, which is a major limitation since molecular interactions within neurons are extremely dynamic, both spatially and temporally. Furthermore, once hypotheses are formed, they are tested in the laboratory, which allows measurement or visualization only of small area or time point. Computer modeling and simulation of the interactions can go well beyond static pathway maps and will allow scientists not only to visualize molecular interactions, but to test hypotheses in the computer before going into the laboratory. Effective computer modeling would accelerate research and reduce the occurrence of "negative data." The few molecular dynamics simulation platforms to date have required significant software development capability and provided very limited representation of interactions. Other simulation platforms have made headway in predicting interactions between neurons but have yet to tackle molecular pathways within a neuron.

BRIEF SUMMARY OF THE INVENTION

Techniques and systems are disclosed for enabling a simulation environment for experimental design. Techniques and systems model the interactions of a configuration of molecules inside a biological structure or system, such as a cell or virtual test tube, using message-based techniques to communicate between molecules proximal to one another in a virtual 3-D geometric space.

Certain implementations include techniques and systems for distributed processing of the individual molecular interactions across a plurality of work nodes.

Some embodiments include techniques and systems for storing detailed information about the current state of the simulation of the biological model for each discrete time slice. This enables the ability for a 4-D (three spatial dimensions and the temporal dimension) playback/review of any particular spatial or temporal focus area of the simulation.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION OF THE INVENTION

Figure 1:
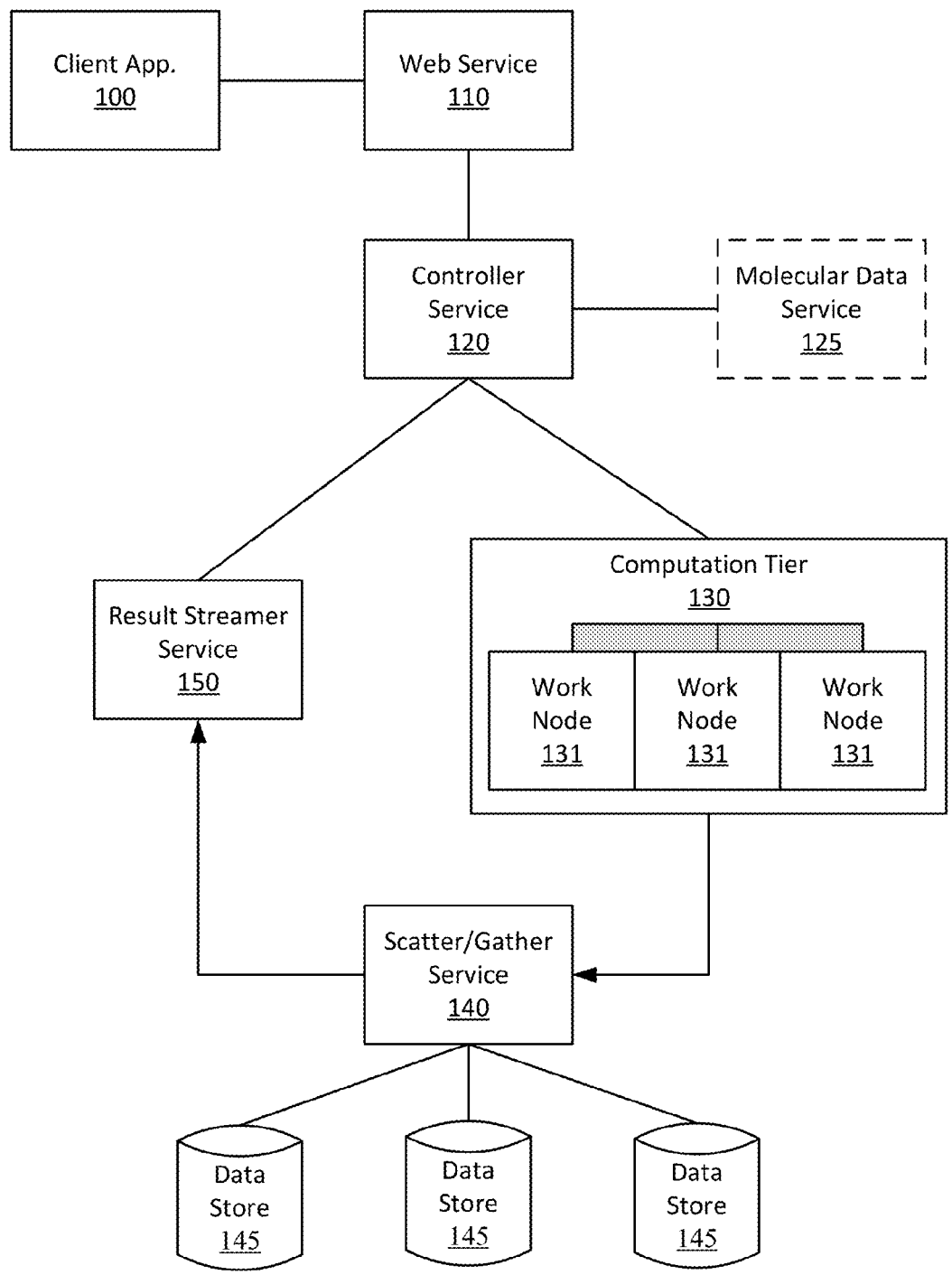
FIG. 1 shows an example component environment in which the described techniques and systems can be implemented.

Techniques and systems are disclosed for enabling a simulation environment for experimental design. Techniques and systems model the interactions of a configuration of molecules inside a biological structure or system, such as a cell, using message-based techniques to communicate between molecules proximal to one another in a virtual 3-D geometric space. The simulation environment allows the understanding, replication, and prediction of biological interactions for various purposes including but not limited to the creation of disease models and development of therapeutic targets. In some cases, unanticipated biological interactions may be discovered which can assist in predicting adverse drug reactions or side-effects well before costly clinical trials begin.

Certain simulation systems such as Monte Carlo Cell (MCell) model the behavior of components in the model stochastically (i.e., movements are assumed to be chaotic and are computed, e.g., with Monte Carlo algorithms), whereas other simulation systems such as Virtual Cell (VCell) determine the behavior of model components through complex differential equations. Technical features described herein enable a biologically realistic, deterministic modeling architecture, in which each entity responds to surrounding stimuli with a scalar response, that is neither stochastic nor evaluates partial differential equations. Advantageously, this deterministic and scalar modeling technique allows very complex systems to be modeled with realistic computational resources and also allows detailed activity data to be stored that can be later analyzed for insight.

Certain implementations include techniques and systems for distributed processing of the individual molecular interactions across a plurality of work nodes. Embodiments of these techniques and systems may divide the virtual 3-D geometric space into geometric portions in accordance with the availability of work nodes. In a simulation environment where the number of different types of molecules can exceed 10,000, this further technical capability enables the technical effect of making complex interactions computable with a reasonably available number of computational resources.

Certain implementations include techniques and systems for storing detailed information about the current state of the simulation of the biological model for each discrete time slice (i.e., action cycle). The storage of the current state of the simulation for every action cycle enables the ability for a 4-D (three spatial dimensions and the temporal dimension) playback/review of any particular spatial or temporal focus area of the simulation. Certain implementations include a 3-D graphical user interface for depicting and replaying the interaction of the molecules over a specified time period.

In some embodiments, the biological structure modeled in the simulation environment is a cell, such as a neuron of the central or peripheral nervous system. While neurons are specifically exemplified herein, other cell types may be modeled in the simulation environment. Cells that may be modeled in the simulation environment can range in plasticity from totipotent or pluripotent stem cells (e.g., adult or embryonic), precursor or progenitor cells, to highly specialized cells, such as those of the nervous system (e.g., neurons and glia). Stem cells can be obtained from a variety of sources, including fetal tissue, adult tissue, umbilical cord blood, peripheral blood, bone marrow, and brain, for example. As used herein, the root term "embryo" is intended to include the morula, blastocyst, gastrula, and neurula.

Stem cells are believed to have immense potential for therapeutic purposes for numerous diseases. Stem cells have been derived from numerous donor sources, including, but not limited to, embryonic, blast, tissue-derived, blood, and cord-blood cells; organ-derived progenitor cells; and bone marrow stromal cells; among others. Such stem cells can be differentiated along numerous pathways to produce virtually any cell type. From a therapeutic perspective, stem cells may be useful for the treatment of a vast array of disorders. Examples of neurological disorders that can potentially be treated with stem cells include Parkinson's disease, Alzheimer's and Huntington's diseases, ALS, stroke, demyelinating disorders, epilepsy, head trauma, and spinal cord injury. Cloned cells, fertilized ova, and non-fertilized gametes can also be modeled.

Other cells that can be modeled include, but are not limited to, neural cells, including dopaminergic neurons from the substantia nigra, ventral tagmental area or median eminence of fetal, neonatal, and adult origins; glial cell lines from various areas of the brain including mesencephalon and striatum, of fetal, neonatal, and adult origins; GABAergic cells of various areas of the brain, including striatum or cortex, of fetal, neonatal, and adult origins; cholinergic neurons from various areas of the brain including the hippocampus, Magnocellular forebrain nucleus of fetal, neonatal, and adult origins; glutamatergic cells of various areas of the brain, including striatum or cortex, of fetal, neonatal, and adult origins, adrenergic and noradrenergic neurons derived from the chromaffin cells or locus coeruleus of embryonic, neonatal, or adult origins, and serotonergic neurons derived from the raphe nuclei of embryonic, neonatal, or adult origins. Glial cells of various regions, including mesencephalon, striatum, cortex, subcortical white matter, spinal cord, or Schwann cells, of fetal, neonatal, and adult origins.

As will be understood by one of skill in the art, there are over 200 cell types in the human body, including those disclosed by disclosed by Spier R. E. et al., eds., (2000) *The Encyclopedia of Cell Technology*, John Wiley & Sons, Inc., and Alberts B. et al., eds., (1994) *Molecular Biology of the Cell*, 3$^{rd}$ ed., Garland Publishing, Inc., e.g., pages 1188-1189. Any of these cells may be modeled in the simulation environment. A non-comprehensive list of cell types that may potentially be modeled is provided in Table 1 herein.

The cell to be modeled in the simulation environment may be of any species. Thus, the cell may be a human cell, or a non-human eukaryotic cell or prokaryotic cell. The modeled cell may be a mammalian cell, reptile cell, amphibian cell, or fish cell, plant cell, yeast cell or bacterial cell, for example.

The cell to be modeled may be a genetically modified cell or non-genetically modified cell. The cell to be modeled can be a normal cell or diseased cell, such as a cancer cell. The cell may be a primary cell or cell of a cell line.

Furthermore, the biological model can be a "virtual test tube" rather than a specific cell type. A virtual test tube is a 3-D geometric space in which a researcher can combine a set of molecules of any desired molecule type and concentration. A virtual test tube might be used, for example, in the early phases of research when the researcher wants to experiment with interactions between a smaller set of molecule types than typically found in a cell.

Molecule types that can be modeled can include, for example, biomolecules that are endogenous or exogenous to the cell (biologics), as well as new or experimental compounds or molecules, such as small molecule drugs under study (typically less than 1,000 daltons). Biomolecules include polypeptides (proteins and peptides), amino acids, lipids, carbohydrates, nucleic acids, nucleotides, viruses, and other molecules that can be produced by cells. Gene therapies may alter the dynamics of protein generation inside the cell, which can also be modeled.

Certain implementations include the ability for the user to select specific molecules from a databank for interaction. Some implementations allow the user to upload the structure of a molecule (e.g., a drug or therapy) being studied for its effect on the molecular interactions within the cell.

FIG. 1 shows an example component environment in which the described techniques and systems can be implemented. One or more components in the example environment may operate to perform techniques or processes described in FIG. 2, for example.

In FIG. 1, a user/client 100, such as a browser application, that displays a user interface for interaction with the simulation environment may connect to a web service 110. The client application 100 can be implemented as a stand-alone application, browser-based application, mobile app, for example. The web service 110 can provide user interface and management functions to the user/client 100. The web service 110 connects to a controller service 120 that performs processing and scheduling services for executing a molecular interaction model within the simulation environment.

A controller service 120, in some embodiments, performs scheduling, control, and coordination processes for a simulation of a biological model. In a typical web service environment, numerous user/client applications can be simultaneously connected to the web service for a simulation. Thus, a controller service 120 may be processing and returning results for many simulations, each modeling different molecular interactions.

Figure 2:
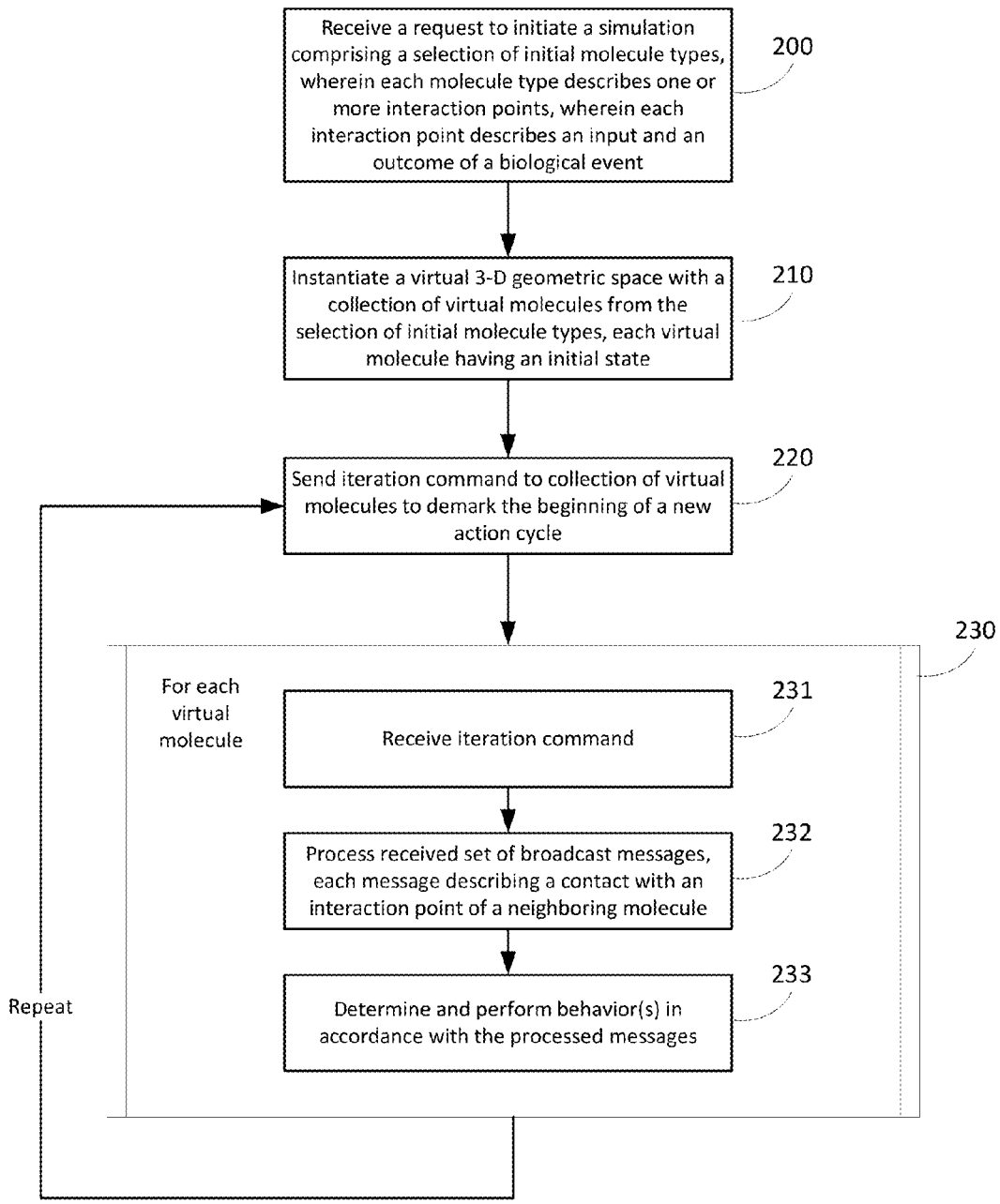
FIG. 2 shows an example process flow used in some embodiments of a simulation environment for experimental design.

As described in more detail in the example process flow of FIG. 2, a controller service 120 receives a request to initiate a simulation of a biological model. The request includes one or more types of molecules under simulation. The controller service instantiates a virtual 3-dimensional (3-D) space to contain the collection of virtual molecules and initializes the virtual molecules with an initial state.

The controller service 120 may optionally connect to a molecular data service 125 to obtain information about the types of molecules that are modeled in the simulation environment. This information can include, for example, the molecular weights of proteins, their reactions, and 3-D visual representations of molecules that can be used to render the molecules graphically. The molecular data service can be one or more of a private database or a free/commercial molecular data service, such as UniProt or the RCSB Protein Data Bank. UniProt is an accessible database of protein sequence and functional information, many entries being derived from genome sequencing projects. RCSB PDB provides information about the 3-D shape of proteins, nucleic acids, and complex assemblies.

In some embodiments, the molecular data service 125 is one or more pathway databases such as KEGG pathway database, WikiPathways, Reactome, NCI-Nature_Pathway_Interaction_Database (a.k.a., NCI Nature Pathway Interaction Database), PhosphoSitePlus, BioCyc_database_collecttion, Human_Protein_Reference_Database, PANTHER (Proetin Analysis Through Evolutionary Relationships), TRANSFAC (Transcription Factor Database), MiRTArBase, DrugBank, Recon X, Comparative_Toxicogenomics_Database (CTD), National Center for Biotechnology Information (NCBI), and Pathway_commons.

In some embodiments, the controller service 120 apportions subsets or sub-regions of the virtual 3-D space by dividing the requested biological model into geometric portions sized to efficiently utilize the available work nodes. The controller service 120 can interact with a computation tier 130 that includes one or more work nodes 131 for processing subsets or sub-regions of the molecular model represented by the geometric portions.

In some embodiments, the computation tier 130, or constituent work nodes 131, interacts with a scatter/gather service 140 capable of distributed storage of the state of the biological model across one or more data stores 145. The distributed storage capability enables large quantities of detailed simulation data to be stored without causing a bottleneck to simulation performance. An example of a scatter/gather service using distributed data stores implements the APACHE HADOOP software framework. Commercial providers of such services include MICROSOFT®, GOOGLE®, IBM®, CLOUDERA®, HORTONWORKS® and AMAZON®.

To view the results or data associated with a requested simulation, the user/client 100 interacts with the web service 110 to request a "view" of all or of subsets of the running molecular interaction model and one or more data sets such as graphical or chart-based representations. A result streamer service 150 may request a subset of the state of a biological model via the scatter/gather service 140 that the result streamer service 150 provides to the controller service 120 for presentation in a user/client 100 via the web service 110. The user/client 100 can view the molecular interaction model, for example, as a 3-D visual rendering of molecules moving in a virtual 3-D space.

In certain embodiments, system components (all or in part) combine to form a modeling platform accessible via programmatic methods through an application programming interface (API). For example, the controller service 120 can be accessed by a web service 110 or other user/client applications 100 via API. An API is generally a set of programming instructions and standards for enabling two or more applications to communicate with each other. An API is an interface implemented by a program code component or hardware component (hereinafter "API-implementing component") that allows a different program code component or hardware component (hereinafter "API-calling component") to access and use one or more functions, methods, procedures, data structures, classes, and/or other services provided by the API-implementing component. An API can define one or more parameters that are passed between the API-calling component and the API-implementing component. The API and related components may be stored in one or more computer readable storage media. An API is commonly implemented as a set of Hypertext Transfer Protocol (HTTP) request messages and a specified format or structure for response messages according to a REST (Representational state transfer) or SOAP (Simple Object Access Protocol) architecture.

FIG. 2 shows an example process flow used in some embodiments of a simulation environment for experimental design. Certain steps of the process flow may be implemented, for example, by a controller service 120 as described in FIG. 1.

Processing begins with the receipt of a request to initiate a simulation comprising a selection of initial molecule types (200). Initiation of the simulation can occur, for example, when a client application 100 sends a request to begin a new simulation. For instance, the user of the client application can be presented with a graphical interface that allows the user to make a selection of molecule types for interaction in the simulation.

As used herein, a "molecule type" is prototype or definition of a molecule. A "virtual molecule" is an individual instance of a molecule type instantiated in the virtual model. For example, a virtual molecule of MAOA is a single instance of the molecule type MAOA. Furthermore, there may be many virtual molecules of MAOA present in a simulation, each of which has various differing attributes like position and velocity.

In many cases, the molecule types have been previously curated, having interaction points that were pre-defined. For instance, the user may initiate a request by selecting an existing cellular model, such as a model of a neuron, that contains a base set of molecule types. Furthermore, the choice of a cellular model might imbue the model with substructures of the cell, such as organelles, which can be represented in the virtual model by the plurality of molecular types the organelle produces. The user of the client application may have the option to modify the molecule types in the existing cellular model in order to view the interactions between various subsets of virtual molecules.

The user can in some cases build on existing models by adding new molecule types. For example, if a researcher wants to perform a simulation of how the microphysiology of a neuron is affected by the introduction of a new drug being tested, the researcher can add, via an interface of a client application, a new molecule type for the drug that defines aspects or parameters of the drug. The researcher can then initiate a simulation to see and/or gather data about the interactions between existing molecules in the neuron and the new drug.

Having received a selection of molecule types, a collection of virtual molecules is instantiated within a virtual 3-D geometric space (210). A virtual 3-D geometric space may be implemented in certain embodiments as a 3-dimensional array where each "cell" (or matrix, or position) in the array contains exactly zero or one virtual molecule. The virtual 3-D geometric space may also be implemented as points connected by various kinds of geometric entities, such as triangles, polygons, lines, or curves. The way the points are connected forms a "mesh" of a particular virtual geometry, for example a sphere representing a biological cell. 3-D gaming and graphics engines, for example Unity3d, Blender, Nvidia CUDA tool kit or Unreal may be used to design and render the virtual 3-D geometric space to a display. The virtual 3-D geometric space can represent, for example, the interior space of a cell or a virtual test tube in which interactions can take place.

A molecule type has one or more interaction points, each of which describes a possible interaction (e.g., a biological reaction or biological event) between itself and other molecule types. An interaction point describes an "input" of the interaction, which can include one or more molecule types (or interactors), and an output, which can include one or more outcome molecule types. An interaction between molecules takes the form:

$$Molecule_1 + Molecule_{(2 \ldots n)} \rightarrow Molecule_{(1 \ldots m)}.$$

For an interaction to occur, all the molecules on the left side of the equation must be present and are transformed by the biological event into the molecules on the right side of the equation. Representing this interaction as an interaction point, the molecules on the left side of the equation are the input and the molecules on the right side of the equation are the outcome. Examples of such biological events include enzymatic conversions and the formation of complexes (with or without byproduct molecules). A biological event can represent part of one or more biological pathways. A biological pathway is a series of actions among molecules of a cell that leads to a certain product or a change in the cell (e.g., at the genomic, transcriptomic, or proteomic level). Common types of biological pathways include metabolic pathway, genetic pathways, and signal transduction pathways, all of which can be modeled.

A biological pathway can trigger assembly of new molecules, such as fats, carbohydrates, or proteins. A biological pathway may involve interactions between molecules that are associated with, or contained within, various cellular organelles including, but not limited to, the plasma membrane, cytoplasm, mitochondria, lysosomes, endosomes, vesicles, nucleus, nucleolus, endoplasmic reticulum, golgi apparatus, ribosomes, and cytoskeleton. Biological pathways can also turn genes on and off, or induce a cell to migrate. Biological pathways can act over short or long anatomical distances. For example, some cells send signals to neighboring cells to repair localized damage, and other cells produce hormones that can travel through the blood and lymphatic system to other cells. Two examples of types of interactions are shown below:

VPS35+VPS25→VPS35·VPS29            Binding Example:

DA+MAOA+$H_2O$+$O_2$→DOPAC+
   MAOA+$H_2O_2$                       Enzymatic Example:

In some embodiments, system components such as a controller service can accept proposed new interaction points to be evaluated in simulation. These proposed new interaction points may be entered, in some cases, via an interface of the client application. The facility to upload new interaction points describing new biochemical reactions allows the simulation environment to grow in sophistication as scientific research progresses.

Instantiation of the virtual geometric space with the collection of virtual molecules refers to creating an instance of one or more virtual molecules of each of the initial molecule types and placing them at a place in the array representing the geometric space. Each virtual molecule is initialized or instantiated with an initial state, and each virtual molecule has the interaction points of the molecule type from which the virtual molecule was derived.

In some cases, the initial state expresses certain physical characteristics of the individual virtual molecule that may influence the interaction behavior of the molecule within the virtual 3-D geometric space. Physical characteristics can include properties such as mass, initial position, and initial velocity. The mass may, for example, be derived from the molecular weight of the molecule type obtained from a molecular data service 125. An individual virtual molecule's initial position and initial velocity within the geometric space might be initialized to a random value. As the virtual molecules begin to move around the 3-D geometric space during a simulation, the initial state and/or physical characteristics may be used by a physics or graphics engine to compute the physical consequences of collisions between virtual molecules.

The activity of a simulation in the model begins by sending a periodic iteration command to the collection of virtual molecules to demark the beginning of a new action cycle (220). A periodic iteration command may be sent, for example, by the controller service 120 on a timed interval to act as a clock or metronome by which the particular simulation run performs its processing. The length of the timed interval may be adjustable, in some cases by the user via the client application 100, and in some cases by the controller service 120, depending on the type of biological model and/or the particular selection of molecule types being simulated. During each action cycle, each virtual molecule conducts the activities and performs the behaviors appropriate to its molecule type, movements, and proximity to other virtual molecules (230).

A sub-process flow depicting the activities of each virtual molecule is shown as part of FIG. 2. The periodic iteration command demarking the beginning of a new action cycle is received by a virtual molecule in the simulation (231). Receipt of the command initiates the processing of a set of broadcast messages received from neighboring molecules, each of which describes a contact with an interaction point of a neighboring molecule (232).

A "message," as described herein, refers to a communication transmitted between entities in the simulation system. The message describes information about the state or activities of an entity such as a virtual molecule. A mechanism for exchanging messages can be implemented in a variety of ways in a virtual system, as a practitioner in the art will recognize. For example, an event-based mechanism may be implemented using a simple stack to which every entity publishes its messages; other entities review the messages in the stack and pull the message if it is addressed to them. In some embodiments, the controller service may receive all messages from all virtual molecules, determine to which destination virtual molecules each message pertains based on their proximity to the sender, and then direct one or more further instructions to the destination virtual molecules.

In some cases, a contact described by a broadcast message can include a collision with a neighboring virtual molecule. A collision can occur when one virtual molecule attempts to move into a "cell" in the 3-D array representing the geometric space that is currently occupied by another virtual molecule. When one virtual molecule attempts to move into the cell of another virtual molecule, either or all of the molecules may transmit a broadcast message indicating a collision.

Sometimes, a contact described by a broadcast message can include receiving notification of a biological event occurring in the other virtual molecule, such as becoming activated with a prescribed affinity. A characteristic of the biological event, such as its type or strength, may determine the distance at which neighboring virtual molecules can receive the messages. As a simple example, a virtual molecule that becomes activated with an affinity of x may broadcast a message that is receivable by neighboring virtual molecules that are one unit away in the 3-D array; whereas, a virtual molecule that becomes activated with an affinity of 2x may broadcast a message that is receivable by neighboring virtual molecules that are two units away.

A virtual molecule can receive more than one broadcast message describing contact with more than one neighboring molecule. In some embodiments, a virtual molecule processes the broadcast messages by reviewing the inputs of each of its interaction points and determining whether a broadcast message was received from each of the molecule types described in the input molecules. If the receiving virtual molecule receives a message from a virtual molecule of each molecule type, then that interaction point is selected as an operative interaction point.

Having processed the received set of broadcast messages, the virtual molecule determines that zero or more interactions have occurred. Interaction points may be ranked or prioritized in some implementations so that a single interaction may be chosen when the inputs of more than one interaction point match the received messages. In some cases, a single interaction may be chosen at random from a set of interaction points having met all their input criteria. In other cases, the received messages do not meet all the input criteria of any interaction point, and hence no interaction point will be chosen. Further, sometimes no broadcast messages are received by a virtual molecule and thus no interaction point will be chosen.

The virtual molecule now determines and performs one or more behaviors in accordance with the processed messages (233). Possibilities for behaviors of a virtual molecule in some embodiments can include, for example, interaction point outcome behaviors, movement behaviors, sending a message to describe a biological event, modifying a "state" or parameter of the virtual molecule, as well as "taking no action."

If a virtual molecule has interacted with one or more neighboring virtual molecules via an interaction point, then a kind of behavior can include transformation of the moving virtual molecule from one molecule type to another molecule type. In some specific instances, new virtual molecules may be created, and, in some instances, molecules may be removed from the simulation. For example, in the enzymatic interaction,

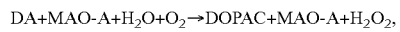

$$DA+MAO\text{-}A+H_2O+O_2 \rightarrow DOPAC+MAO\text{-}A+H_2O_2,$$

DA is transformed into DOPAC and water and oxygen are transformed into peroxide in the presence of an enzyme, MAO-A, that remains unchanged by the reaction. In other words, in this example reaction, two virtual molecules change their molecule type, one remains the same, and one virtual molecule is removed.

Sometimes, a behavior can include modifying the velocity or vector of motion of a virtual molecule within the virtual 3-D geometric space. In some instances, a collision occurs because one virtual molecule attempts to move into a cell in the 3-D array that is occupied by another molecule. In such a case, the virtual molecules determine whether interaction points creating an outcome reaction are applicable, as previously described, but they also have a physical consequence upon the movement of the virtual molecules within the virtual space. Based on such factors as the "mass," velocity, and vector of motion of the moving virtual molecule and the occupying virtual molecule, a new velocity and/or vector of motion may be determined for the virtual molecule. For example, a moving virtual molecule might "displace" the virtual molecule in the cell, or the moving virtual molecule might "bounce back," modifying the vector of motion for both molecules. In some cases, the motion vectors of the virtual molecules may be calculated using a "physics engine" of 3-D modeling software, for example, Unity3d.

Sometimes, a behavior can include sending an outbound broadcast message describing a particular biological event. A biological event can encompass the full range of biological and chemical modifications that affect the secondary, tertiary, and quaternary structure of the biological molecule. A biological event can be a post-translational modification, such as, e.g., methylation, phosphorylation, ubiquitination, N-methylation, O-glycosylation, and N-glycosylation. A biological event can include such events as activation with an affinity, deactivation, binding, releasing, transforming, misfolding, truncation, and degradation. As noted, these broadcast messages identify such information as the sender and the type of biological event and can be received by neighboring virtual molecules to determine interaction points between the sending and receiving virtual molecules.

A type of behavior can also include modifying one or more parameter of the virtual molecule. Each virtual molecule has "state" (a collection of parameters, attributes, or properties) describing important aspects of the virtual molecule, for example, its mass, velocity, and the gene that expresses the molecule in a cell. These parameters, and others, may be modified as a consequence of interactions with other molecules.

A behavior can also include "taking no action." In any given action cycle, a virtual molecule might not contact or interact with another virtual molecule and therefore may idle.

After performing the determined behavior(s), the virtual molecule awaits the next periodic iteration command, repeating the sub-process flow (230).

Some embodiments provide a system for balancing the processing activities in the simulation across a number of available work nodes. The system may be implemented, among other ways, in the example component environment described in FIG. 1. Techniques performed by the system can be performed, for example, by the controller service 120 and the computation tier 130 with its multiplicity of work nodes 131.

Techniques for balancing the processing activities in the simulation include dividing the virtual 3-D geometric space of a given simulation into one or more "geometric portions." A geometric portion is any subset of the "cells" of the virtual 3-D geometric space. For example, if the entire virtual 3-D geometric space is represented as a "cube" that is 100 cells wide, 100 cells deep, and 100 cells high, a geometric portion of that space could be, for example, 5×5×5 cells. Each geometric portion contains the virtual molecules resident in the physical space defined by the virtual model.

The virtual 3-D geometric space may be divided into appropriately sized geometric portions in accordance with the available work nodes. The available work nodes may be determined with reference to the number of servers or processors available in a given installation environment. The "load" of a work node can be can be determined statically or dynamically. For example, a work node can have a static setting for the maximum number of geometric portions it may calculate; until the work node's actual work load exceeds the maximum, it is an "available" work node. A work node can also have a dynamic setting, in which the maximum number of geometric portions it may calculate is a factor of the number of processing cores in the work node. In some instances, the availability of a work node is determined by a performance characteristic of the work node, such as the percentage of processor load at the current time, or other loading factors.

Once the number of available work nodes is known, the geometric portions may be created, sized, and distributed to the work nodes for processing.

Certain embodiments provide systems and techniques for storing a current state of the simulation of the biological model for each new action cycle. The current state of the simulation can include such information as the number and type of virtual molecules present in the current action cycle. The current state can also include activity data detailing the activity of each virtual molecule in every action cycle. The activity data can contain a representation of the received set of broadcast messages for the virtual molecule. The activity data can also contain one or more current parameter of the virtual molecule, as well as a representation of the one or more behaviors determined and performed during the action cycle.

In some cases, the activity data may be stored on one or more data stores 145, as shown in FIG. 1. A group of distributed data stores 145 can be managed, for example, by a scatter/gather service 140 which is capable of distributing the storage load among multiple data stores. Storage of the activity data across multiple data stores can provide the facility to store the extreme volume of interactions and details that may only be present during a complex simulation.

Any or all of the activity data of the individual virtual molecules in the simulation can provide valuable data points for scientific research. The activity data can be analyzed to construct reports and produce trend analyses of levels of the different molecule types and the locations or interactions of molecules. Data analytics strategies may be used to mine this detailed activity data for potential targets, as well as to identify knowledge gaps for future research. Analysis of activity data may provide insight into unforeseen effects or interactions between molecules, or may help to validate the efficacy of molecules or treatments under study.

The storage of the current state of the simulation for every action cycle enables the ability for 4-D "playback" of any aspect or "focus area" of the simulation. In certain embodiments, this capability can be used to focus on the specific behaviors of certain selections of the virtual molecules, the focus area being defined, for example, by its spatial and temporal coordinates.

Figure 3:
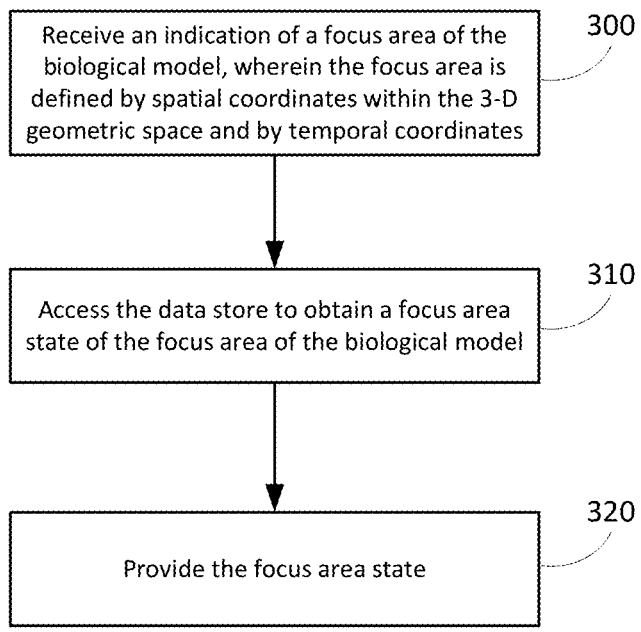
FIG. 3 shows an example process flow for a 4-D playback of simulation results.

FIG. 3 shows an example process flow used in some embodiments of a 4-D playback of simulation results. After receiving a request for a particular focus area defining particular spatial and temporal coordinates (300), the data store can be accessed to obtain the state of the simulation of the biological model at those spatial and temporal coordinates (310). These results may be provided back to the requestor, for example as a 3-D rendering in a graphical display, or in "results stream" of data (320). In some exemplary implementations, a results streamer service 150 may perform techniques related to receiving a request for a focus area of the simulation of the biological model (300), accessing the data store (310), and providing the focus area state data back to the requestor (320).

Figure 4:
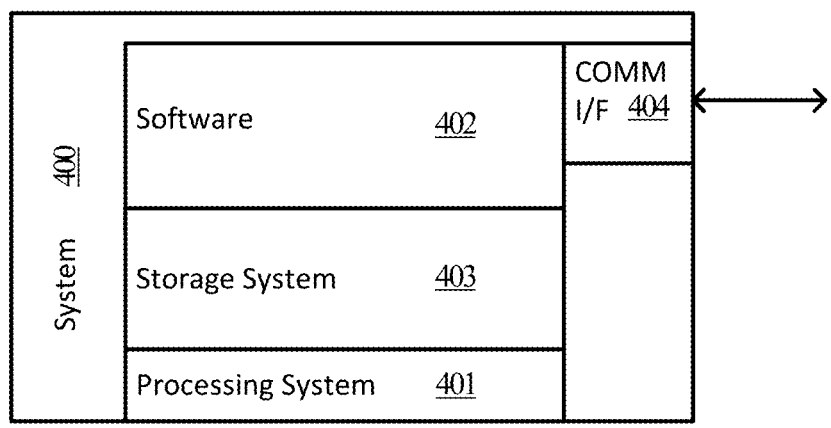
FIG. 4 shows a block diagram illustrating components of a computing device or system used in some embodiments of the subject invention.

FIG. 4 shows a block diagram illustrating components of a computing device or system used in some implementations. For example, any computing device operative to run a client application 100, web service 110, controller service 120, computation tier 130 and associated work nodes 131, scatter/gather service 140 and associated data storage devices 145, result streamer service 150 (from FIG. 1), or intermediate devices facilitating interaction between other devices in the environment, may each be implemented as described with respect to system 400, which can itself include one or more computing devices. The system 400 can include one or more blade server devices, standalone server devices, personal computers, routers, hubs, switches, bridges, firewall devices, intrusion detection devices, mainframe computers, network-attached storage devices, and other types of computing devices. The server hardware can be configured according to any suitable computer architectures such as a Symmetric Multi-Processing (SMP) architecture or a Non-Uniform Memory Access (NUMA) architecture.

The system 400 can include a processing system 401, which may include a processing device such as a central processing unit (CPU) or microprocessor and other circuitry that retrieves and executes software 402 from storage system 403. Processing system 401 may be implemented within a single processing device but may also be distributed across multiple processing devices or sub-systems that cooperate in executing program instructions.

Examples of processing system 401 include general purpose central processing units, application specific processors, and logic devices, as well as any other type of processing device, combinations, or variations thereof. The one or more processing devices may include multiprocessors or multi-core processors and may operate according to one or more suitable instruction sets including, but not limited to, a Reduced Instruction Set Computing (RISC) instruction set, a Complex Instruction Set Computing (CISC) instruction set, or a combination thereof. In certain embodiments, one or more digital signal processors (DSPs) may be included as part of the computer hardware of the system in place of or in addition to a general purpose CPU.

Storage system 403 may comprise any computer readable storage media readable by processing system 401 and capable of storing software 402. Storage system 403 may include volatile and nonvolatile, removable and non-removable media implemented in any method or technology for storage of information, such as computer readable instructions, data structures, program modules, or other data.

Examples of storage media include random access memory (RAM), read only memory (ROM), magnetic storage (e.g., disks, tapes, devices), optical storage (e.g., disks, devices), CDs, DVDs, flash memory, phase change memory, or any other suitable storage media. Certain implementations may involve either or both virtual memory and non-virtual memory. In no case do storage media consist of a propagated signal. In addition to storage media, in some implementations storage system 403 may also include communication media over which software 402 may be communicated internally or externally.

Storage system 403 may be implemented as a single storage device but may also be implemented across multiple storage devices or sub-systems co-located or distributed relative to each other. Storage system 403 may include additional elements, such as a controller, capable of communicating with processing system 401.

Software 402 may be implemented in program instructions and among other functions may, when executed by system 400 in general or processing system 401 in particular, direct system 400 or processing system 401 to operate as described herein for enabling a simulation environment for experimental design. Software 402 may provide program instructions that implement controller service, computation tier with work nodes, scatter/gather service, web service, client application, or result streamer service. Software 402 may implement on system 400 components, programs, agents, or layers that implement in computer or machine-readable processing instructions the methods described herein as performed by the controller service, computation tier with work nodes, scatter/gather service, web service, client application, or result streamer service.

Software 402 may also include additional processes, programs, or components, such as operating system software or other application software. Software 402 may also include firmware or some other form of machine-readable processing instructions executable by processing system 401.

In general, software 402 may, when loaded into processing system 401 and executed, transform system 400 overall from a general-purpose computing system into a special-purpose computing system customized to enable a simulation environment for experimental design. Indeed, encoding software 402 on storage system 403 may transform the physical structure of storage system 403. The specific transformation of the physical structure may depend on various factors in different implementations of this description. Examples of such factors may include, but are not limited to, the technology used to implement the storage media of storage system 403 and whether the computer-readable storage media are characterized as primary or secondary storage.

System 400 may represent any computing system on which software 402 may be staged and from where software 402 may be distributed, transported, downloaded, or otherwise provided to yet another computing system for deployment and execution, or yet additional distribution.

It should be noted that many elements of system 400 may be included in a system-on-a-chip (SoC) device. These elements may include, but are not limited to, the processing system 401, a communications interface 404, and even elements of the storage system 403 and software 402.

In embodiments where the system 400 includes multiple computing devices, one or more communications networks may be used to facilitate communication among the computing devices. For example, the one or more communications networks can include a local, wide area, or ad hoc network that facilitates communication among the computing devices. One or more direct communication links can be included between the computing devices. In addition, in some cases, the computing devices can be installed at geographically distributed locations. In other cases, the multiple computing devices can be installed at a single geographic location, such as a server farm or an office.

A communication interface 404 may be included, providing communication connections and devices that allow for communication between system 400 and other computing systems (not shown) over a communication network or collection of networks (not shown) or the air. Examples of connections and devices that together allow for inter-system communication may include network interface cards, antennas, power amplifiers, RF circuitry, transceivers, and other communication circuitry. The connections and devices may communicate over communication media to exchange communications with other computing systems or networks of systems, such as metal, glass, air, or any other suitable communication media. The aforementioned communication media, network, connections, and devices are well known and need not be discussed at length here.

Figure 5:
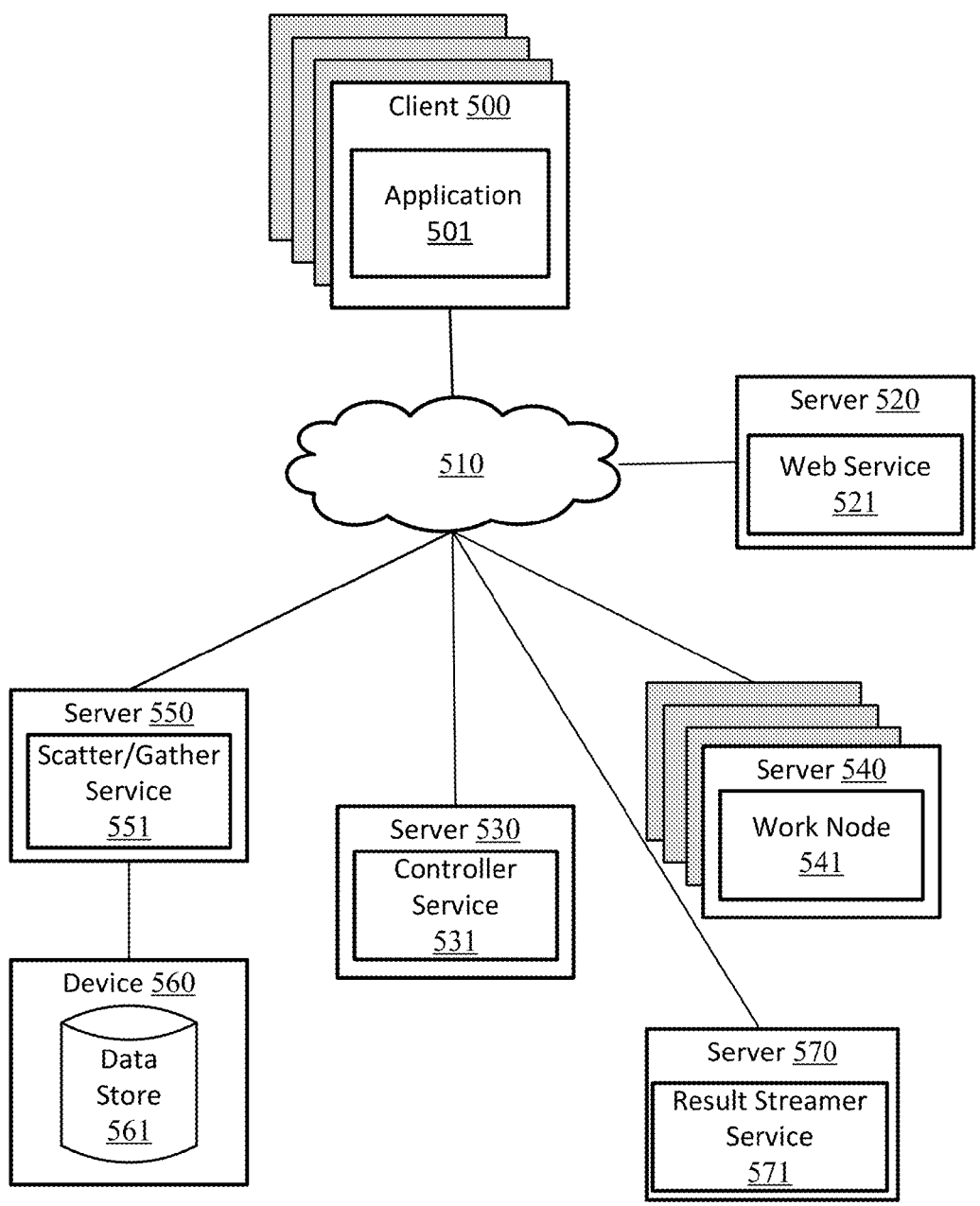
FIG. 5 illustrates an example system architecture in which an implementation of techniques for a simulation environment for experimental design may be carried out.

FIG. 5 illustrates an example system architecture in which an implementation of techniques for a simulation environment for experimental design may be carried out. In the example illustrated in FIG. 5, a client application 501 can be implemented on a client device 500, which may be a particular instantiation of a system 400 as described with respect to FIG. 4, and may be or include computing systems such as a laptop, desktop, tablet, mobile phone, and the like. Many client applications may be present in a given environment (represented by the gray shadow boxes behind 500).

Communications and interchanges of data between components in the environment may take place over network 510. The network 510 can include, but is not limited to, a cellular network (e.g., wireless phone), a point-to-point dial up connection, a satellite network, the Internet, a local area network (LAN), a wide area network (WAN), a WiFi network, an ad hoc network, an intranet, an extranet, or a combination thereof. The network may include one or more connected networks (e.g., a multi-network environment) including public networks, such as the Internet, and/or private networks such as a secure enterprise private network.

A web service 521 may be implemented as software or hardware (or a combination thereof) on server 520, which also may be an instantiation of system 400. Web service 521 may receive requests from client application 501 and direct them to controller service 531.

A controller service 531 may be implemented as software or hardware (or a combination thereof) on server 530, which also may be an instantiation of system 400. Controller service 531 may receive communications from web service 521 and interact with other system components as described above.

One or more work nodes 541 may be implemented as software or hardware (or a combination thereof) on one or more server 540, which also may be an instantiation of system 400. Work nodes 541 may receive communications from controller service 531 and interact with other system components as described above.

Work nodes 541 may direct storage operations to a scatter/gather service 551, which may be implemented on server 550 (which may itself be an instantiation of system 400 or aspects thereof). Scatter/gather service 551 may itself use one or more distributed data stores 561 hosted on one or more device 560, each of which may be instantiations of system 400.

A result streamer service 571 may be implemented as software or hardware (or a combination thereof) on server 570, which also may be an instantiation of system 400. Result streamer service 571 may receive communications from web service 521 or application 501, as well as interact with other system components as described above.

The features and functions of a controller service 531, result streamer service 571, or web service 521 may be callable by an application 501 through an API. Indeed, any or all of the interactions between environmental components herein may be initiated and performed as API calls. The API and related components may be stored in one or more computer readable storage media (e.g., storage media such as hard drives, magnetic disks, solid state drives, RAM, flash, CDs, DVDs and the like).

FIG. 5 shows system components operative on separate devices 500, 520, 530, 540, 550, 560, and 570. It should be noted, however, that any number of and even all of the software components described above as client application 501, web service 521, controller service 531, work node 541, scatter gather service 551, data store 561, and result streamer service 571 need not be run on separate devices, and may indeed be run on the same device.

Alternatively, or in addition, the functionality, methods and processes described herein can be implemented, at least in part, by one or more hardware modules (or logic components). For example, the hardware modules can include, but are not limited to, application-specific integrated circuit (ASIC) chips, field programmable gate arrays (FPGAs), system-on-a-chip (SoC) systems, complex programmable logic devices (CPLDs) and other programmable logic devices now known or later developed. When the hardware modules are activated, the hardware modules perform the functionality, methods and processes included within the hardware modules.

TABLE 1

Examples of Cells for Modeling

Keratinizing Epithelial Cells keratinocyte of epidermis
basal cell of epidermis
keratinocyte of fingernails and toenails
basal cell of nail bed
hair shaft cells
medullary
cortical
cuticular
hair-root sheath cells
cuticular
of Huxley's layer
of Henle's layer
external
hair matrix cell Cells of Wet Stratified Barrier Epithelia surface epithelial cell of stratified squamous epithelium of cornea tongue, oral cavity, esophagus, anal canal, distal urethra, vagina
basal cell of these epithelia
cell of urinary epithelium Epithelial Cells Specialized for Exocrine Secretion cells of salivary gland
mucous cell
serous cell
cell of von Ebner's gland in tongue
cell of mammary gland, secreting milk
cell of lacrimal gland, secreting tears
cell of ceruminous gland of ear, secreting wax
cell of eccrine sweat gland, secreting glycoproteins
cell of eccrine sweat gland, secreting small molecules
cell of apocrine sweat gland
cell of gland of Moll in eyelid
cell of sebaceous gland, secreting lipid-rich sebum
cell of Bowman's gland in nose
cell of Brunner's gland in duodenum, secreting alkaline solution of mucus and enzymes
cell of seminal vesicle, secreting components of seminal fluid, including fructose
cell of prostate gland, secreting other components of seminal fluid
cell of bulbourethral gland, secreting mucus
cell of Bartholin's gland, secreting vaginal lubricant
cell of gland of Littré, secreting mucus
cell of endometrium of uterus, secreting mainly carbohydrates
isolated goblet cell of respiratory and digestive tracts, secreting mucus
mucous cell of lining of stomach
zymogenic cell of gastric gland, secreting pepsinogen
oxyntic cell of gastric gland, secreting HCl
acinar cell of pancreas, secreting digestive enzymes and bicarbonate
Paneth cell of small intestine, secreting lysozyme
type II pneumocyte of lung, secreting surfactant
Clara cell of lung Cells Specialized for Secretion of Hormones cells of anterior pituitary, secreting
growth hormone
follicle-stimulating hormone
luteinizing hormone
prolactin
adrenocorticotropic hormone
thyroid-stimulating hormone TABLE 1-continued Examples of Cells for Modeling cell of intermediate pituitary, secreting melanocyte-stimulating hormone
cells of posterior pituitary, secreting
oxytocin
vasopressin
cells of gut and respiratory tract, secreting
serotonin
endorphin
somatostatin
gastrin
secretin
cholecystokinin
insulin
glucagons
bombesin
cells of thyroid gland, secreting
thyroid hormone
calcitonin
cells of parathyroid gland, secreting
parathyroid hormone
oxyphil cell
cells of adrenal gland, secreting
epinephrine
norepinephrine
steroid hormones
mineralocorticoids
glucocorticoids
cells of gonads, secreting
testosterone
estrogen
progesterone
cells of juxtaglomerular apparatus of kidney
juxtaglomerular cell
macula densa cell
peripolar cell
mesangial cell Epithelial Absorptive Cells in Gut, Exocrine Glands, and Urogenital Tract brush border cell of intestine
striated duct cell of exocrine glands
gall bladder epithelial cell
brush border cell of proximal tubule of kidney
distal tubule cell of kidney
nonciliated cell of ductulus efferens
epididymal principal cell
epididymal basal cell Cells Specialized for Metabolism and Storage hepatocyte
fat cells (e.g., adipocyte)
white fat
brown fat
lipocyte of liver Epithelial Cells Serving Primarily a Barrier Function, Lining the Lung, Gut, Exocrine Glands, and Urogenital Tract type I pneumocyte
pancreatic duct cell
nonstriated duct cell of sweat gland, salivary gland, mammary gland, etc.
parietal cell of kidney glomerulus
podocyte of kidney glomerulus
cell of thin segment of loop of Henle
collecting duct cell
duct cell of seminal vesicle, prostate gland, etc.

Epithelial Cells Lining Closed Internal Body Cavities vascular endothelial cells of blood vessels and lymphatics (e.g., microvascular cell)
fenestrated
continuous
splenic
synovial cell
serosal cell
squamous cell lining perilymphatic space of ear
cells lining endolymphatic space of ear
squamous cell
columnar cells of endolymphatic sac
with microvilli
without microvilli

TABLE 1-continued

Examples of Cells for Modeling

"dark" cell
vestibular membrane cell
stria vascularis basal cell
stria vascularis marginal cell
cell of Claudius
cell of Boettcher
choroid plexus cell
squamous cell of pia-arachnoid
cells of ciliary epithelium of eye
pigmented
nonpigmented
corneal "endothelial" cell
Ciliated Cells with Propulsive Function of respiratory tract
of oviduct and of endometrium of uterus
of rete testis and ductulus efferens
of central nervous system
Cells Specialized for Secretion of Extracellular Matrix epithelial:
ameloblast
planum semilunatum cell of vestibular apparatus of ear
interdental cell of organ of Corti
nonepithelial:
fibroblasts
pericyte of blood capillary (Rouget cell)
nucleus pulposus cell of intervertebral disc
cementoblast/cementocyte
odontoblast/odontocyte
chondrocytes
of hyaline cartilage
of fibrocartilage
of elastic cartilage
osteoblast/osteocyte
osteoprogenitor cell
hyalocyte of vitreous body of eye
stellate cell of perilymphatic space of ear
Contractile Cells skeletal muscle cells
red
white
intermediate
muscle spindle-nuclear bag
muscle spindle-nuclear chain
satellite cell
heart muscle cells
ordinary
nodal
Purkinje fiber
Cardiac valve tissue
smooth muscle cells
myoepithelial cells:
of iris
of exocrine glands
Cells of Blood and Immune System red blood cell (erythrocyte)
megakaryocyte
macrophages
monocyte
connective tissue macrophage
Langerhan's cell
osteoclast
dendritic cell
microglial cell
neutrophil
eosinophil
basophil
mast cell
plasma cell
T lymphocyte
helper T cell
suppressor T cell
killer T cell
B lymphocyte
IgM
IgG
IgA
IgE
killer cell
stem cells and committed progenitors for the blood and immune system
Sensory Transducers photoreceptors
rod
cones
blue sensitive
green sensitive
red sensitive
hearing
inner hair cell of organ of Corti
outer hair cell of organ of Corti
acceleration and gravity
type I hair cell of vestibular apparatus of ear
type II hair cell of vestibular apparatus of ear
taste
type II taste bud cell
smell
olfactory neuron
basal cell of olfactory epithelium
blood pH
carotid body cell
type I
type II
touch
Merkel cell of epidermis
primary sensory neurons specialized for touch
temperature
primary sensory neurons specialized for temperature
cold sensitive
heat sensitive
pain
primary sensory neurons specialized for pain
configurations and forces in musculoskeletal system
proprioceptive primary sensory neurons
Autonomic Neurons cholinergic
adrenergic
peptidergic
Supporting Cells of Sense Organs and of Peripheral Neurons supporting cells of organ of Corti
inner pillar cell
outer pillar cell
inner phalangeal cell
outer phalangeal cell
border cell
Hensen cell
supporting cell of vestibular apparatus
supporting cell of taste bud
supporting cell of olfactory epithelium
Schwann cell
satellite cell
enteric glial cell
Neurons and Glial Cells of Central Nervous System neurons
glial cells
astrocyte
microglia
oligodendrocyte
Lens Cells anterior lens epithelial cell
lens fiber
Pigment Cells melanocyte
retinal pigmented epithelial cell
iris pigment epithelial cell TABLE 1-continued Examples of Cells for Modeling Germ Cells oogonium/oocyte
spermatocyte
Spermatogonium
blast cells
fertilized ovum Nurse Cells ovarian follicle cell
Sertoli cell
thymus epithelial cell (e.g., reticular cell)
placental cell All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A method for enabling a simulation environment for experimental design, the method comprising:
   receiving a request to initiate a simulation of a biological model of a cell having organelles (cell model), wherein the request comprises a selection of initial entities comprising one or more organelles of the cell model and one or more molecule types contained within, or associated with the one or more organelles of the cell model, wherein each entity has one or more interaction points, and wherein each interaction point describes an input and an outcome of a biological event;
   instantiating the initial entities of the request to a data structure representing a virtual three-dimensional (3-D) geometric space, wherein the instantiated data structure comprises the selection of initial entities at locations within the virtual 3-D geometric space, wherein the instantiated data structure describes an initial state of each instantiated entity and describes a plurality of available behaviors for each instantiated entity, wherein the initial state of each instantiated entity comprises each of, a mass of the instantiated entity, a number of copies of the instantiated entity, an initial position of each instantiated instance of the entity within the virtual 3-D geometric space, and an initial velocity of each instance of the instantiated entity, and wherein one or more of the available behaviors is to be determined and performed upon an interaction event;
   dividing the virtual 3-D geometric space into one or more geometric portions sized in accordance with available work nodes;
   distributing the one or more geometric portions to the available work nodes for processing, wherein each geometric portion comprises a subset of the instantiated entities;
   performing a periodic iteration to evaluate each interaction point of each instantiated entity within the virtual 3-D geometric space to identify interactions with other instantiated entities that would result in performance of a determined behavior, wherein each periodic iteration command demarks the beginning of a new action cycle;
   wherein, in the periodic iteration, each of the instantiated entities:
      updates its position and velocity within the virtual 3-D geometric space;
      identifies occurrence of a collision, if present, with other instantiated entities and performs one or more determined behaviors from among the plurality of available behaviors, wherein the plurality of available behaviors includes, at least each of: binding or releasing of an instantiated entity, changing the secondary, tertiary, or quaternary structure of an instantiated entity, and transforming an instantiated entity to a different entity type;
      performs the determined one or more behaviors; and
      waits for a next periodic iteration command.

2. The method of claim 1, wherein the plurality of available behaviors further includes, at least each of:
   adding a new instantiated entity to the virtual 3-D geometric space,
   removing one or more of the instantiated entities from the virtual 3-D geometric space,
   modifying a velocity or vector of motion of one or more of the instantiated entities within the virtual 3-D geometric space, and
   modifying one or more parameters of one or more of the instantiated entities.

3. The method of claim 2, wherein the biological event is selected from the group consisting of activation, deactivation, binding, releasing, transforming, methylation, phosphorylation, ubiquitination, N-methylation, O-glycosylation, N-glycosylation, misfolding, truncation, degradation, and biological/chemical modifications affecting the secondary, tertiary, and quaternary structure of a molecule.

4. The method of claim 1, further comprising storing, in a data store, a current state of the simulation of the cell model for the new action cycle.

5. The method of claim 4, wherein the current state of the simulation of the cell model comprises activity data for each instantiated entity for each action cycle.

6. The method of claim 5, wherein the activity data comprises one or more of:
   one or more current parameters; and
   a representation of the one or more behaviors.

7. The method of claim 1, wherein the cell model is a neuron model.

8. The method of claim 1, wherein the selection of initial entities comprises at least one experimental molecule type, or at least one molecule type selected from a repository, or both.

9. The method of claim 1, wherein one of the one or more interaction points comprises a proposed interaction point.

10. A system for enabling a simulation environment for experimental design, the system comprising:
    program instructions stored on one or more non-transitory computer readable storage media for a controller service that, when executed by a processing system, direct the processing system to:
       in response to receiving a request to initiate a simulation of a biological model of a cell having organelles (cell model), wherein the request comprises a selection of initial entities comprising one or more organelles of the cell model and one or more molecule types contained within, or associated with the one or more organelles of the cell model, wherein each entity has one or more interaction points, and wherein each interaction point describes an input and an outcome of a biological event:

instantiate the initial entities of the request to a data structure representing a virtual three-dimensional (3-D) geometric space, wherein the instantiated data structure comprises the selection of initial entities at locations within the virtual 3-D geometric space, wherein the instantiated data structure describes an initial state of each instantiated entity and describes a plurality of available behaviors for each instantiated entity, wherein the initial state of each instantiated entity comprises each of: a mass of the instantiated entity, a number of copies of the instantiated entity, an initial position of the instantiated entity within the virtual 3-D geometric space, and an initial velocity of the instantiated entity, and wherein one or more of the available behaviors is to be determined and performed upon an interaction event;

divide the virtual 3-D geometric space into one or more geometric portions sized in accordance with available work nodes;

distribute the one or more geometric portions to the available work nodes for processing, wherein each geometric portion comprises a subset of the instantiated entities;

send a periodic iteration command to a processing work node, wherein each periodic iteration command demarks the beginning of a new action cycle; and one or more work nodes, each work node having second program instructions stored on second one or more computer readable storage media that, when executed by second processing system, direct the processing system to:

in response to receiving the periodic iteration command, instruct each instantiated entity in the subset of instantiated entities to:

update the instructed instantiated entity's position and velocity within the virtual 3-D geometric space, identify occurrence of a collision, if present, with other instantiated entities and perform one or more determined behaviors from among the plurality of available behaviors, wherein the plurality of available behaviors includes, at least each of: binding or releasing of an instantiated entity, changing the secondary, tertiary, or quaternary structure of an instantiated entity, and transforming an instantiated entity to a different entity type;

store, in a data store, activity data for the instantiated entity for the new action cycle.

11. The system of claim 10, wherein the controller service further comprises program instructions that, when executed by the processing system, direct the processing system to:

in response to receiving an indication of a focus area of the cell model, wherein the focus area is defined by spatial coordinates within the virtual 3-D geometric space and by temporal coordinates:

access the data store to obtain a focus area state of the focus area of the cell model; and provide the focus area state.

12. The system of claim 10, wherein the plurality of available behaviors further includes, at least each of:

adding a new instantiated entity to the virtual 3-D geometric space, and removing one or more of the instantiated entities from the virtual 3-D geometric space, modifying a velocity or vector of motion of one or more of the instantiated entities within the virtual 3-D geometric space, and modifying one or more parameters of one or more of the instantiated entities.

13. The system of claim 12, wherein the biological event is selected from the group consisting of activation, deactivation, binding, releasing, transforming, methylation, phosphorylation, ubiquitination, N-methylation, O-glycosylation, N-glycosylation, misfolding, truncation, degradation, and biological/chemical modifications affecting the secondary, tertiary, and quaternary structure of a molecule.

14. The system of claim 10, wherein a current state of the simulation of the cell model comprises the activity data for each instantiated entity for each action cycle.

15. The system of claim 14, wherein the activity data comprises one or more of:

one or more current parameters; and a representation of the one or more behaviors.

16. The system of claim 10, wherein the cell model is a model of a neuron.

17. The system of claim 10, wherein the selection of initial entities comprises at least one experimental molecule type, or at least one molecule type selected from a repository, or both.

18. The system of claim 10, wherein one of the one or more interaction points comprises a proposed interaction point.

19. The method of claim 1, wherein the virtual 3-D geometric space is rendered to a display.

20. The method of claim 1, wherein the request to initiate the simulation is received via a processing system.

21. The system of claim 10, wherein the virtual 3-D geometric space is rendered to a display.

22. The system of claim 10, wherein the request to initiate the simulation is received via a processing system.

* * * * *

UNITED STATES PATENT AND TRADEMARK OFFICE
CERTIFICATE OF CORRECTION

PATENT NO. : 9,805,159 B2  
APPLICATION NO. : 14/790400  
DATED : October 31, 2017  
INVENTOR(S) : Bahareh Behrouz and Andrew David Lee Page 1 of 1

It is certified that error appears in the above-identified patent and that said Letters Patent is hereby corrected as shown below:

In the Claims

<u>Column 19,</u>  
Line 54, In Claim 1 "each of, a mass" should read --each of: a mass--.

Signed and Sealed this  
Twenty-fifth Day of September, 2018

Andrei Iancu  
*Director of the United States Patent and Trademark Office*